United States Patent
Koop

(10) Patent No.: US 9,810,624 B2
(45) Date of Patent: Nov. 7, 2017

(54) SPECTROSCOPIC SENSOR DEVICE AND METHOD FOR OPERATING A SPECTROSCOPIC SENSOR DEVICE

(71) Applicant: Robert Bosch GmbH, Stuttgart (DE)

(72) Inventor: Paul Koop, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/307,414

(22) PCT Filed: Mar. 5, 2015

(86) PCT No.: PCT/EP2015/054623
§ 371 (c)(1),
(2) Date: Oct. 28, 2016

(87) PCT Pub. No.: WO2015/169472
PCT Pub. Date: Nov. 12, 2015

(65) Prior Publication Data
US 2017/0052113 A1 Feb. 23, 2017

(30) Foreign Application Priority Data

May 6, 2014 (DE) ........................ 10 2014 208 382

(51) Int. Cl.
*G01N 21/25* (2006.01)
*G01N 21/3504* (2014.01)
(Continued)

(52) U.S. Cl.
CPC ............ *G01N 21/3504* (2013.01); *G01J 3/12* (2013.01); *G01J 3/2803* (2013.01); *G01J 3/42* (2013.01);
(Continued)

(58) Field of Classification Search
CPC ........ G01J 3/28; G01J 3/12; G01J 3/42; G01J 3/02; G01N 21/3504; G01N 33/00; G01N 33/004; G01N 21/25
See application file for complete search history.

(56) References Cited

U.S. PATENT DOCUMENTS 8,559,721 B1 10/2013 Bartholomew
2008/0251724 A1* 10/2008 Baliga ....................... G01J 3/02
250/338.5

FOREIGN PATENT DOCUMENTS

DE 102006049260 A1 4/2008
DE 102009027134 A1 12/2010
(Continued)

OTHER PUBLICATIONS

International Search Report, dated May 11, 2015, of the corresponding PCT application PCT/EP2015/054623 filed Mar. 5, 2015.

*Primary Examiner* — Abdullahi Nur
(74) *Attorney, Agent, or Firm* — Norton Rose Fulbright US LLP; Gerard Messina

(57) ABSTRACT

A spectroscopic sensor device comprising an absorption path for receiving at least one fluid medium that is to be analyzed, an infrared radiation source for sending out infrared radiation into the absorption path, an infrared sensor array that has a multiplicity of pixels that can be individually evaluated, which are fashioned to detect the infrared radiation propagated from the infrared radiation source through the fluid medium as individual pixel measurement signals, and comprising an evaluation device that is fashioned to combine a multiplicity of pixel measurement signals of the pixels and to output them via an individual measurement channel. Furthermore, a method for operating a spectroscopic sensor device is also described.

9 Claims, 3 Drawing Sheets

(51) Int. Cl.
    *G01J 3/42*           (2006.01)
    *G01J 3/28*           (2006.01)
    *G01N 33/00*         (2006.01)
    *G01J 3/12*           (2006.01)

(52) U.S. Cl.
    CPC .... G01N 33/004 (2013.01); *G01J 2003/1213* (2013.01)

(56) References Cited

FOREIGN PATENT DOCUMENTS

| | | |
|---|---|---|
| EP | 1070956 A1 | 1/2001 |
| WO | 0169208 A1 | 9/2001 |

\* cited by examiner

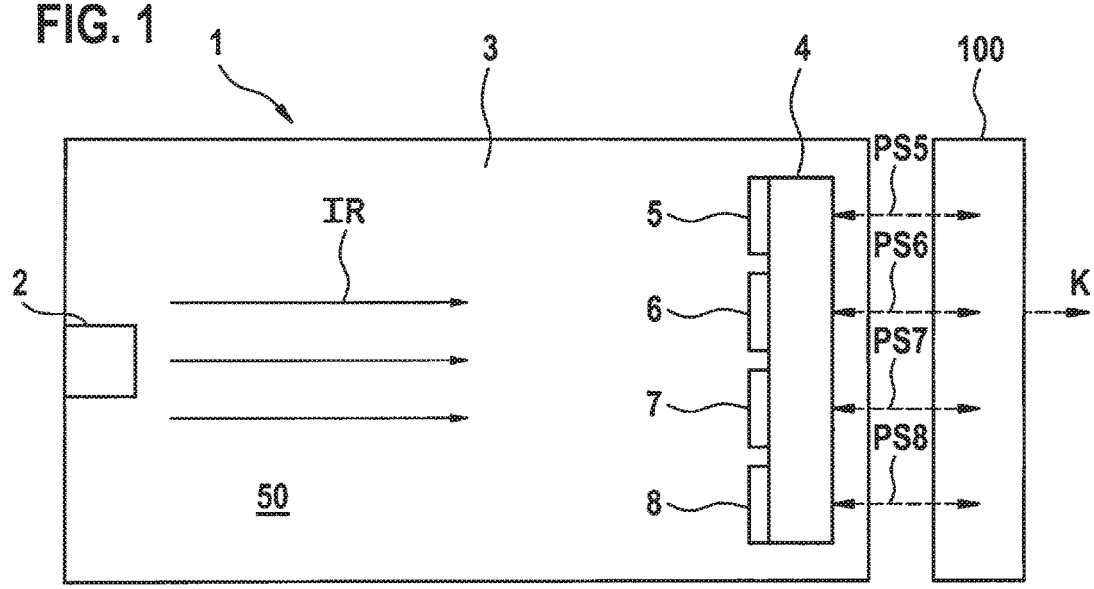
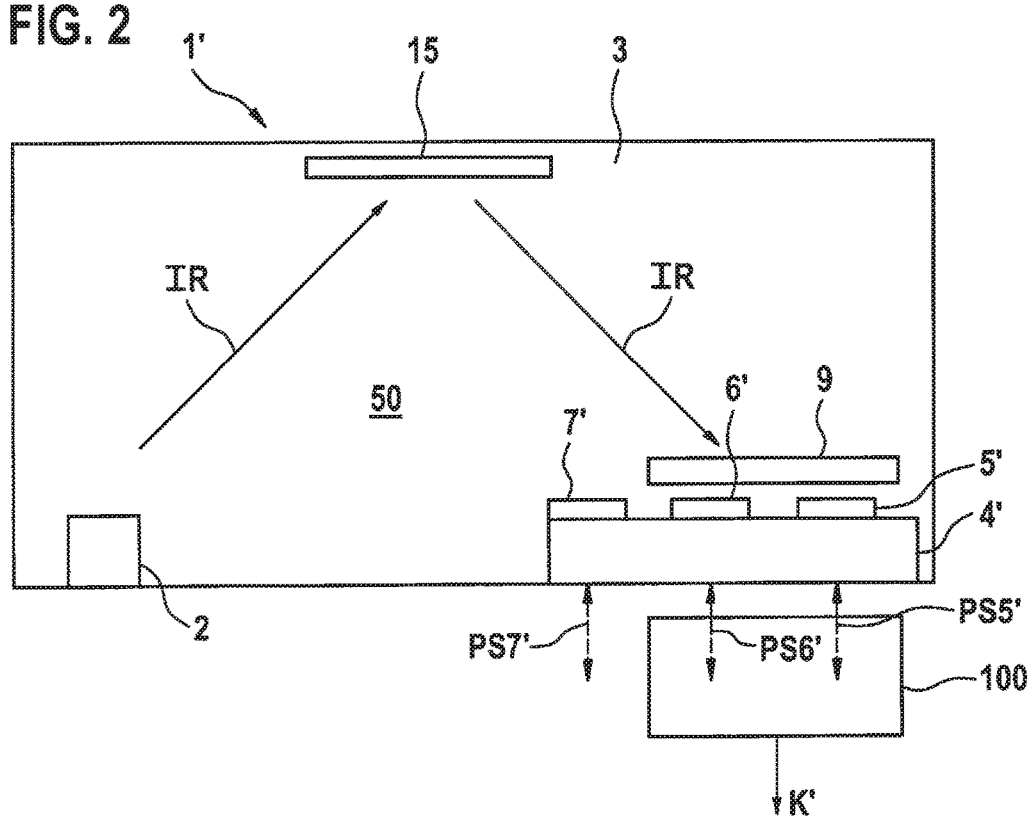

SPECTROSCOPIC SENSOR DEVICE AND METHOD FOR OPERATING A SPECTROSCOPIC SENSOR DEVICE

FIELD

The present invention relates to a spectroscopic sensor device and to a method for operating a spectroscopic sensor device.

BACKGROUND INFORMATION

In fluid media that are to be examined, in particular in gases or liquids, spectroscopic sensors are used to ascertain concentrations of particular substances through the absorption of IR radiation in relevant wavelength ranges.

Conventional spectroscopic sensors generally use a broadband infrared radiator and an infrared detector having one or more detector channels. Standardly, for each gas or liquid species a detector channel is used as measurement channel, and a further detector channel is used as reference channel.

In particular, two-channel detectors for detecting a particular substance are conventional. In such a two-channel detector, a first detector channel is used for the detection of the radiation in a relevant wavelength range, in which an absorption band of the substance to be ascertained or examined is situated, and the second detector channel is used as reference channel for detection in a broader wavelength range. The selection of the wavelength ranges takes place in general through the use of optical filters that are transparent for particular wavelengths, or wavelength ranges.

German Patent Application No. DE 10 2009 027 136 A1 describes a spectroscopic sensor that has an IR radiation source for emanating IR radiation, an absorption path for receiving a gas or liquid, at least one optical filter for the wavelength-selective transmission of the IR radiation moving through the absorption path, and at least one detector for receiving the IR radiation moving through the optical filter and outputting a measurement signal. The IR radiation source and the detector are fastened and contacted on a circuit bearer, and the absorption path is fashioned as the interior compartment of a reflector device that is fastened on the circuit bearer and that has a reflective interior surface, so that a direct transmission of radiation from the IR radiation source to the detector without reflection on the reflector device is prevented.

German Patent Application No. DE 10 2009 027 124 A1 describes a spectroscopic sensor that has an absorption path for receiving a substance that is to be examined, an IR radiation source for emanating IR radiation through the absorption path, a detector device that has at least one first and second detector element for detecting the IR radiation moving through the absorption path and for outputting measurement signals. An evaluation device is provided that receives the measurement signals of the at least two detector elements and ascertains a content of a first medium, the first detector element detecting IR radiation in a first wavelength range and outputting a first measurement signal, the second detector element detecting IR radiation in a second wavelength range differing from the first wavelength range and outputting a second measurement signal. In the first wavelength range there is situated an absorption band of the first medium and of a second medium. In the second wavelength range there is situated an absorption band either of the first medium or of the second medium, the evaluation device receiving the second measurement signal for correcting the first measurement signal.

SUMMARY

The present invention provides a spectroscopic sensor device, and a method for operating a spectroscopic sensor device.

Preferred developments are described herein.

In accordance with the present invention, an infrared sensor array is provided that has a multiplicity of individually evaluable pixels that are fashioned to detect the infrared radiation propagated from the infrared radiation source through the fluid medium as individual pixel measurement signals, an evaluation device being provided that is fashioned to combine a specifiable plurality of pixel measurement signals of the pixels and to output it via a single measurement channel.

Through the use of an infrared sensor array having a plurality of selectable or controllable pixels for a single measurement channel, a simple possibility is created for internal self-analysis for safety-relevant applications.

In particular, sensitivity due to local contamination in the optical path of the measurement path can be reduced or eliminated. In addition, sensitivity to mechanical or other manufacturing tolerances in the production of the sensor device can be reduced. In addition, the measurement sensitivity and the signal-noise ratio of the sensor device are increased through a simultaneous use of a plurality of individually evaluable pixels. In particular, the flexibility for different gases can be improved. The possibilities for correcting the deviations due to environmental influences/aging can also be significantly improved.

As infrared radiation source, for example a broadband radiation source, such as a light bulb or a heated wire, or a narrow-band radiation source such as a light-emitting diode or a laser can be used. The absorption path can be provided with inlet and outlet openings so that the gas or fluid to be examined can flow into the absorption path and out of the absorption path.

According to the present invention, the pixels of one or more pixel regions are provided at least in part with a respective optical filter for wavelength-selective transmission of the infrared radiation.

The evaluation device is fashioned to determine the position of the optical filter or filters. The filter or filters can, for example due to production-related errors, be situated not exactly at the predetermined position on the pixels of the sensor array, so that some pixels are not completely covered by a filter. Through a measurement of the individual pixel measurement signals of the individual pixels, a position determination of the filters on the infrared sensor array can be carried out by the evaluation device. The evaluation device is then for example fashioned to take into account during the combining only pixel measurement signals of pixels that are completely covered by a filter. Pixels and pixel regions that are not covered by a filter are not taken into account by the evaluation device during a measurement. In this way, the measurement precision of the sensor is further increased. The exact position of the filters can be stored in a memory in the evaluation device.

According to a specific embodiment of the present invention, at least two pixels of the infrared sensor array are fashioned to detect a first gas, and are provided with a first optical filter for the wavelength-selective transmission of the infrared radiation. The filter can for example be glued onto the chip cap of the sensor array, and/or can be connected to the chip cap of the sensor array by a mechanical connection, e.g., a screw connection. For example, the sensor array has two rows of pixels and two columns of pixels, at least two of the four pixels being provided with the first filter for wavelength-selective transmission of the infrared radiation. For example, two of these pixels are provided with a filter that lets through infrared radiation only in the wavelength range of the absorption bands of carbon dioxide. These pixels are then used to detect carbon dioxide in the absorption path. An alternative possibility is to apply the specific absorption layers directly on the individual pixels. These absorption layers can be optimized for a particular wavelength, so that the effect of the optical filter results.

According to a further specific embodiment of the present invention, at least two pixels of the sensor array are fashioned to detect a second gas, and are provided with a second optical filter for the wavelength-selective transmission of the infrared radiation. For example, the sensor array has four lines of pixels and four columns of pixels, nine of the sixteen pixels being provided with the second filter for the wavelength-selective transmission of the infrared radiation. For example, nine of these pixels are provided with a filter that lets through infrared radiation only in the wavelength range of the absorption bands of water. These pixels are then used to detect water in the absorption path. The evaluation device can then have a second measurement channel that outputs the combined pixel measurement signals for the second gas.

According to a further specific embodiment of the present invention, at least one pixel of the sensor array is fashioned as a monitoring and compensation pixel. For example, the sensor array has eight lines of pixels and eight columns of pixels, nine of the 64 pixels being provided with the first filter, another nine pixels being provided with the second filter, another nine of the pixels being provided with the reference filter, and the remaining pixels being provided with no filter. The monitoring and compensation pixel is fashioned for example to monitor the output of the infrared radiation source and/or the degree of contamination of the measurement path. An aging of the infrared radiation source and/or a shift of the radiated wavelength range can also be acquired and corrected if warranted using the evaluation device. According to the present invention, this can take place selectively for each individual pixel of the sensor array.

According to a further specific embodiment of the present invention, the evaluation device is fashioned to not take into account pixel measurement signals of pixels in one or more pixel ranges on the basis of at least one specified criterion during the combining of the pixel measurement signals. In this way, the measurement precision can be increased.

According to a further specific embodiment of the present invention, the specified criterion can be that a deviation of the pixel measurement signal from the mean value of the pixel measurement signals is greater than a specified amount. For example, pixel measurement signals of pixels are not taken into account that have a deviation of more than 5%, 10%, 20%, 30%, 40%, or 50% from the mean value of the pixel measurement signals. It is also possible for example for only pixel measurement signals to be taken into account that lie within one standard deviation $\sigma$, two standard deviations $2\sigma$, or three standard deviations $3\sigma$ from the mean value. Influencing factors such as the sensitivity of the individual pixels and/or the offset of the pixel measurement signals of the individual pixels and/or the gain of the individual pixels can be taken into account in the combination of the pixel measurement signals for the individual measurement channel. If these components of the pixel measurement signals deviate too significantly, these individual pixels are not taken into account in a combining of the pixel measurement signals.

According to a further specific embodiment of the present invention, the evaluation device is fashioned in one piece with the sensor array. For example, the evaluation device and the sensor array are fashioned as an ASIC (application-specific integrated circuit). However, the evaluation device can also be fashioned as an external microcontroller and can be coupled with the individual pixels in each case via a sensor line. The sensor array can for example be fashioned from a CCD (charge-coupled device) sensor array, or can be fashioned in CMOS technology. The pixels can also each have a separate evaluation circuit, which, connected together, form the evaluation device.

According to a further specific embodiment of the present invention, the evaluation device is fashioned to modify the gain and/or the offset of the individual pixels. Because the pixels of the sensor array are fashioned so as to be individually controllable, in this way the measurement precision can easily be improved.

The described embodiments and developments can be combined with one another in any desired manner.

BRIEF DESCRIPTION OF THE DRAWINGS

The figures are intended to impart a further understanding of the specific embodiments of the present invention. They illustrate specific embodiments, and, together with the description, are intended to explain the principles and designs of the present invention.

Other specific embodiments, and many of the named advantages, result with regard to the figures. The elements depicted in the figures are not necessarily shown to scale relative to one another.

FIG. 1 shows a schematic sectional image of a spectroscopic sensor device according to a specific embodiment of the present invention.

FIG. 2 shows a schematic sectional image of a spectroscopic sensor device according to a further specific embodiment of the present invention.

In the Figures, identical reference characters designate identical or functionally identical elements, assemblies, or components, unless otherwise indicated.

DETAILED DESCRIPTION OF EXAMPLE EMBODIMENTS

Figure 3:
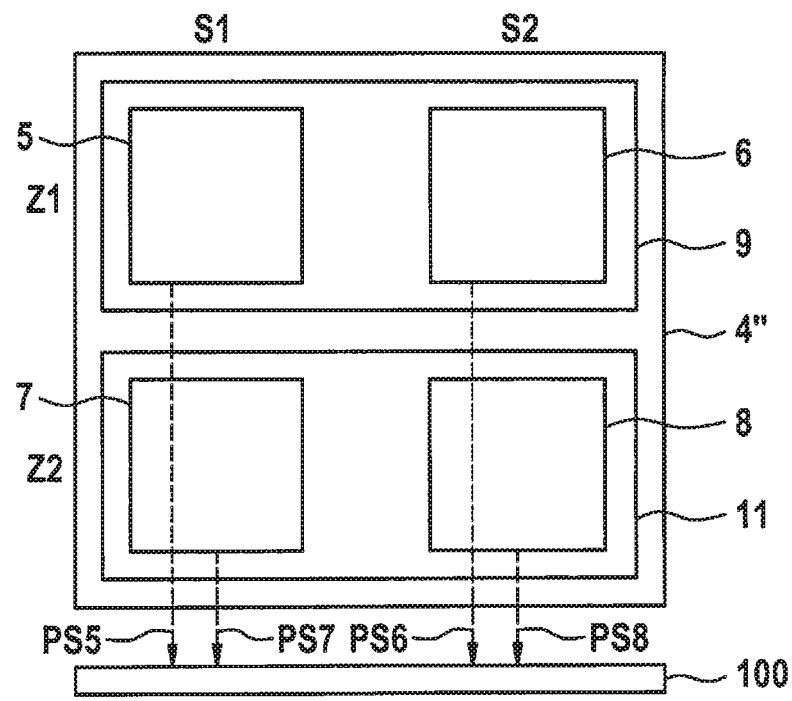
FIG. 3 shows a schematic top view of an infrared sensor array of a spectroscopic sensor device according to a further specific embodiment of the present invention.

FIG. 1 shows a schematic sectional image of a spectroscopic sensor device 1 according to a specific embodiment of the present invention.

Spectroscopic sensor device 1 has an absorption path 3 in which there is situated at least one fluid 50 to be detected, e.g., gaseous carbon dioxide. The one spectroscopic sensor device 1 has an infrared radiation source 2 that is fashioned to radiate infrared radiation IR into absorption path 3. Infrared radiation source 2 can be a broadband radiation source, such as a light-emitting diode or a light bulb, and can emanate electromagnetic radiation in a wavelength range of from approximately 700 nanometers to 2 millimeters, preferably 780 nanometers to 1 millimeter. However, infrared radiation source 2 can also be fashioned as a monochromatic radiation source that emanates only electromagnetic radiation in the absorption range of fluid 50 to be examined.

In addition, spectroscopic sensor device 1 has an infrared sensor array 4 that has a matrix having a multiplicity of individually evaluable and controllable pixels 5, 6, 7, 8, that are fashioned to detect the infrared radiation IR sent out by infrared radiation source 2 and propagated through the fluid as individual pixel measurement signals.

Moreover, spectroscopic sensor device 1 has an evaluation device 100 that is fashioned to combine a multiplicity of individual pixel measurement signals of pixels 5, 6, 7, 8, and to output them via an individual measurement channel K. Spectroscopic sensor device 1 shown in FIG. 1 has four pixels 5, 6, 7, 8, which are each fashioned to be individually evaluable and controllable, and that are coupled with evaluation device 100 via sensor lines PS5, PS6, PS7, and PS8.

According to this specific embodiment of the present invention, evaluation device 100 is designed to not take into account, in the combining of the pixel measurement signals, pixel measurement signals of individual pixels that have a deviation greater than a predetermined amount from the mean value of the pixel measurement signals. This means that if for example pixel 5 and pixel 8 of infrared sensor array 4 supply an errored pixel measurement signal to evaluation device 100 via sensor lines PS5 and PS8, pixels 5 and 8 will not be taken into account in the combining of the pixel measurement signals of infrared sensor array 4, or are switched off by evaluation device 100 via sensor lines PS5 and PS8.

Individual pixels 5, 6, 7, 8 can also be controlled by evaluation device 100 in such a way that for example the pixel measurement signals of pixels 5 and 8 can be corrected. If for example pixels 5 and 8 have an offset error, the offset error of pixels 5 and 8 can be separately corrected. The sensitivity and/or the gain of pixels 5 and 8 can also for example be errored, and corrected as needed by evaluation device 100.

In FIG. 1, evaluation device 100 is fashioned separate from infrared sensor array 4, e.g., as an external microcontroller. However, evaluation device 100 can also be fashioned in one piece with infrared sensor array 4, or can be integrated in the pixels.

In this specific embodiment, the correction function is preprogrammed in evaluation device 100, e.g., in the final check. In a further embodiment, it is possible for the correction function to be subsequently modifiable by an external input device (not shown), or to have a self-adaptation function.

FIG. 2 shows a schematic sectional image of a spectroscopic sensor device 1' according to a further specific embodiment of the present invention. In this specific embodiment, infrared radiation IR of infrared radiation source 2 is deflected toward infrared sensor array 4' via a reflector 15. In this way, absorption path 3 can be lengthened. Pixels 5' and 6' of infrared sensor array 4 supply pixel measurement signals to evaluation device 100, which outputs the combined pixel measurement signals via the single measurement channel K'.

In the depicted specific embodiment, over pixels 5' and 6' there is situated an optical filter 9 that is fashioned for the wavelength-selective transmission of the infrared radiation. For example, filter 9 is fashioned to let through only wavelengths that are relevant for a measurement of carbon dioxide. Filter 9 and the transmission spectrum can be suitably selected depending on the application and the gas to be detected. Filter 9 can be connected to infrared sensor array 4' and the corresponding pixels 5', 6' for example by gluing.

Pixel 7' of infrared sensor array 4', which is not covered by filter 9, can for example be used as reference pixel for compensation, for calibration, or for monitoring the one spectroscopic sensor device 1'. For example, with pixel 7' the output of infrared radiation source 2, or the degree of contamination of reflector 15, can be ascertained.

FIG. 3 shows an exemplary top view of an infrared sensor array 4'' of a spectroscopic sensor device according to a further specific embodiment of the present invention.

In this specific embodiment, infrared sensor array 4'' has two lines of pixels Z1 and Z2 and two columns of pixels S1 and S2. Infrared sensor array 4'' has in this way four quadratically configured pixels 5, 6, 7, and 8. Pixels 5 and 6 are provided with an optical filter 9 that lets through only radiation that lies in the absorption band of carbon dioxide. Pixels 7 and 8 are provided with an optical reference filter 11. Because each pixel 5, 6, 7, and 8 can be controlled individually by evaluation device 100, it can be checked by evaluation device 100 at any time whether the two pixels 5 and 6 for the gas measurement, and/or the two pixels 7 and 8 for the compensation, have different pixel measurement signals. If pixels 5 and 6, or pixels 7 and 8, have a different signal, then an error is present.

This error can for example have its cause in a local contamination by a particle on filter 9 or 11, and/or in a faulty sensor line PS5, PS6, PS7, PS8, and/or in the failure of the evaluation circuit for the respective pixel 5, 6, 7, and 8. Evaluation device 100 can in this way check whether an error is present.

Due to the higher number of pixels, the sensitivity of the measurement for the gas by pixels 5 and 6, and for the reference value by pixels 7 and 8, can be additively increased. In addition, in this way the measurement can be significantly refined. In addition, through this embodiment a defective pixel can be reliably recognized and, if warranted, switched off or corrected by evaluation device 100.

Figure 4:
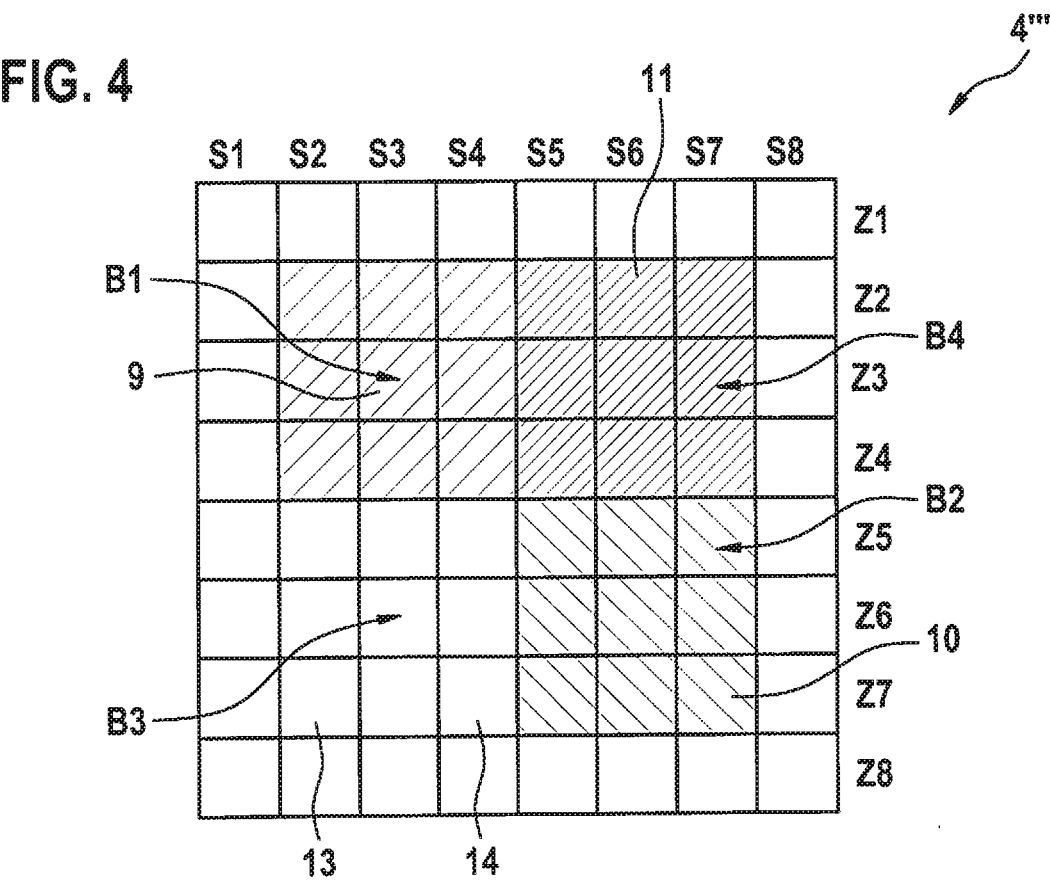
FIG. 4 shows a schematic top view of an infrared sensor array of a spectroscopic sensor device according to a further specific embodiment of the present invention.

FIG. 4 shows an exemplary top view of an infrared sensor array 4''' of a spectroscopic sensor device according to a further specific embodiment of the present invention. In this specific embodiment, infrared sensor array 4''' has eight lines Z1-Z8 of individually evaluable pixels, and eight columns S1-S8 of individually evaluable pixels. In this specific embodiment, infrared sensor array 4'' is fashioned to simultaneously analyze two different gases in absorption path 3.

For example, a first pixel region B1 that includes lines Z2-Z4 and columns S2-S4 is covered by a first optical filter 9. Optical filter 9 can be fashioned to be transparent for wavelengths in the absorption band of carbon dioxide. Pixel range B1 thus includes nine pixels that are individually evaluated and can be outputted via a first measurement channel.

Because these pixels in pixel region B1 are provided with the same filter 9, after the manufacture of spectroscopic sensor device 1 an identical pixel measurement signal must be present at these nine pixels when there is a test. If a significant deviation is determined for a pixel through comparison of the pixel measurement signals of the nine pixels in evaluation device 100, then a defect must be present at this pixel. This pixel can then be excluded during the measurement by evaluation device 100, and after this the functionality can be further fulfilled without errors.

In FIG. 4, it will be seen that infrared sensor array 4''' is provided with different optical filters 9, 10, 11. In addition, pixels of infrared sensor array 4 are not provided with a filter. The pixel regions without filters can be used for particular additional functions, e.g. as reference pixels.

Pixel region B2 is provided with an optical filter 10 whose transmission range is in the range of the water absorption bands. Pixel region B2 includes nine individually evaluable pixels, and extends between lines Z5-Z7 and columns S5-S7. With these pixels, for example the water portion of the gas can be detected and outputted via a second measurement channel.

The pixels that are not provided with a filter, e.g., pixel 13 and pixels 14 in third pixel region B3, can for example be used to monitor the output of infrared radiation source 2 over the lifetime of the spectroscopic sensor device, and to correct it as needed using evaluation device 100.

Fourth pixel region B4, which is situated between lines Z2-Z4 and columns S5-S7, is provided with an optical reference filter 12, and is used to monitor the pixel measurement signals obtained by pixel regions B1 and B2. In pixel region B4 as well, there are situated nine pixels that can be individually evaluated and controlled.

Figure 5:
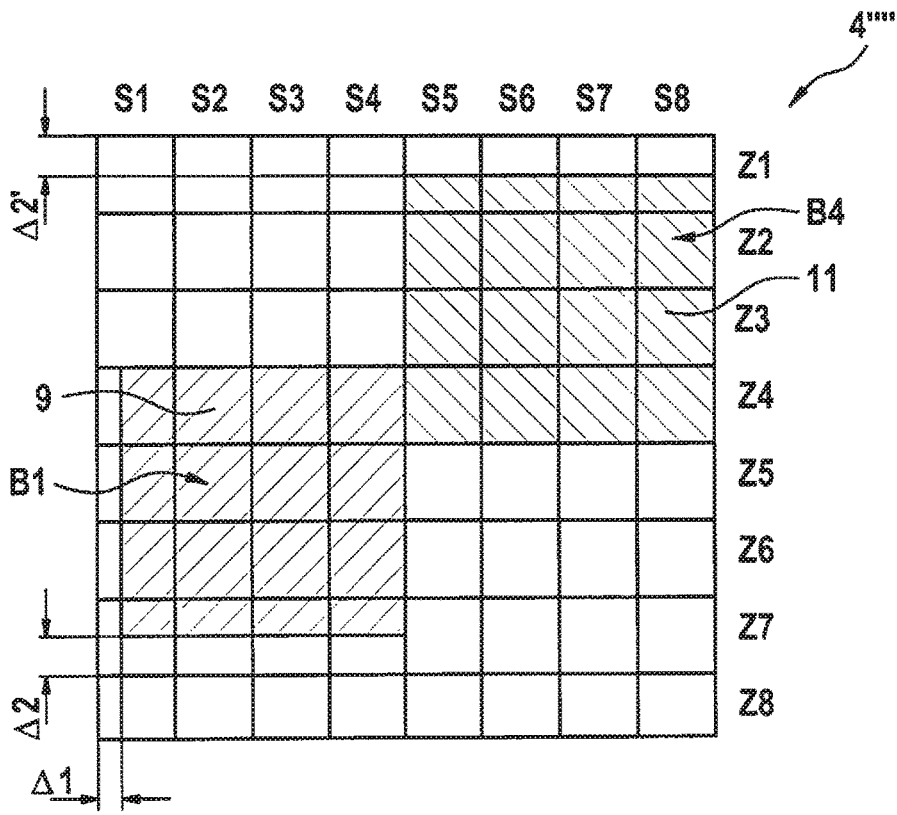
FIG. 5 shows a schematic top view of an infrared sensor array of a spectroscopic sensor device according to a further specific embodiment of the present invention.

FIG. 5 shows an example of a top view of an infrared sensor array 4'''' of a spectroscopic sensor device according to a further specific embodiment of the present invention.

In this specific embodiment, evaluation device 100 can determine the precise position of first optical filter 9 and/or of reference filter 11 on the pixels of infrared sensor array 4, and can contribute to the significant minimization of the demands on the manufacturing tolerances by eliminating wrongly covered pixels from the evaluation.

If, as is shown schematically in FIG. 5, an optical filter 9 is used whose dimension is selected such that it is ensured that at least four pixels are covered, but the position of filter 9 over the pixels is not exactly correct due to manufacturing, then during the evaluation of the pixel measurement signals of the individual pixels the position of the filter can be determined through a comparison of the pixel measurement signals of the individual pixels, and can be stored in a memory in evaluation device 100.

Filter 9 of infrared sensor array 4'''', which is for example transparent for wavelengths in the absorption band of methane, is dimensioned such that it can completely cover nine pixels. If, during manufacture, when optical filter 9 is attached onto infrared sensor array 4'''' there occurs an error in the positioning of filter 9 on the pixels, then using evaluation device 100 it can be checked which of the pixels in the region between lines Z4-Z8 and columns S1-S4 have a pixel measurement signal that is within a specified tolerance. Evaluation device 100 recognizes for example that the pixels in the region between lines Z4-Z6 and in the region between columns S2-S4 each output pixel measurement signals that lie within a tolerance of 10% from the mean value.

Evaluation device 100 recognizes this and, during a measurement of a gas, takes into account only the pixel measurement signals that go out from pixels that are situated in the region between lines Z4-Z6 and in the region between the columns S2-S4.

Because the pixels between lines Z4-Z7 in column S1 are only partly covered by filter 9, because the filter is horizontally offset by Δ1, and the pixels between the columns S1 and S4 in line Z7 are likewise only partly covered by filter 9 because the filter is vertically offset by Δ2, these pixels output a pixel measurement signal to evaluation device 100 that is outside the tolerance limit. The pixels between lines Z4-Z7 in column S1 and between columns S1 and S4 in line Z7 are therefore not taken into account during a measurement.

The precise position of reference filter 11 in pixel region B4 can be determined in an analogous manner. Reference filter 11 is also offset in the vertical direction by Δ2'. Therefore, the pixels between columns S5-S8 in line Z1 are only partly covered by reference filter 11. Evaluation device 100 can therefore determine the precise position of reference filter 11 on the pixels on the basis of the pixel measurement signals obtained from the pixels in pixel region B4, and can take into account only the pixels in the region between lines Z2-Z4 and columns S3-S8.

Figure 6:
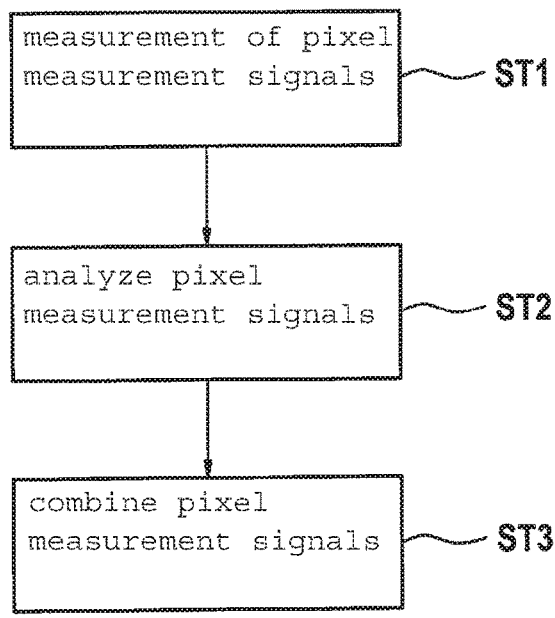
FIG. 6 shows a schematic flow diagram of a method for operating a spectroscopic sensor device according to a further specific embodiment of the present invention.

FIG. 6 shows a schematic flow diagram of a method for operating a spectroscopic sensor device according to a further specific embodiment of the present invention.

In a first method step ST1, there takes place a measurement of the pixel measurement signals of the pixels in one or more pixel regions, in each case with a multiplicity of pixels of an infrared sensor array.

In a second method step ST2, there takes place an analysis of the pixel measurement signals on the basis of at least one specified criterion. For example, there takes place a calculation of the mean value of the pixel measurement signals and an ascertaining of a respective deviation therefrom of the individual pixel measurement signals.

In a third method step ST3, there takes place a combining of the pixel measurement signals of the individual pixels in a respective region, taking into account the result of the analysis. For example, pixel measurement signals of individual pixels that have a deviation greater than a predetermined amount from the mean value of the pixel measurement signals are not taken into account in the combining.

Although the present invention has been described above on the basis of preferred exemplary embodiments, it is not limited thereto, but rather can be modified in many ways. In particular, the present invention can be modified in many ways without departing from the core of the present invention.

What is claimed is:

1. A spectroscopic sensor device, comprising:
   an absorption path for receiving at least one fluid medium that is to be analyzed;
   an infrared radiation source for sending out infrared radiation into the absorption path;
   an infrared sensor array that has a multiplicity of pixels that can be individually evaluated, which are fashioned to detect the infrared radiation propagated from the infrared radiation source through the fluid medium as individual pixel measurement signals, the pixels of one or more pixel regions of the infrared sensor array being provided at least partly with a respective optical filter for the wavelength-selective transmission of the infrared radiation; and
   an evaluation device that is fashioned to combine a multiplicity of pixel measurement signals of the pixels and to output them via an individual measurement channel, the evaluation device being fashioned to determine the position of the optical filter or filters.

2. The spectroscopic sensor device as recited in claim 1, wherein at least two pixels of the infrared sensor array are fashioned to detect a first gas, and being provided with a first optical filter for the wavelength-selective transmission of the infrared radiation.

3. The spectroscopic sensor device as recited in claim 2, wherein at least two pixels of the infrared sensor array are fashioned to detect a second gas, and being provided with a second optical filter for the wavelength-selective transmission of the infrared radiation.

4. The spectroscopic sensor device as recited in claim 1, wherein at least one pixel of the infrared sensor array is fashioned as a monitoring and compensation pixel.

5. The spectroscopic sensor device as recited in claim 1, wherein the evaluation device is fashioned to not take into account pixel measurement signals of pixels in one or more pixel regions of the infrared sensor array on the basis of at least one specified criterion during the combining of the pixel measurement signals.

6. The spectroscopic sensor device as recited in claim 5, wherein the specified criterion being that a deviation of the pixel measurement signal from a mean value of the pixel measurement signals is greater than a prespecified amount.

7. The spectroscopic sensor device as recited in claim 1, wherein the evaluation device is fashioned in one piece with the infrared sensor array.

8. The spectroscopic sensor device as recited in claim 1, wherein the evaluation device is fashioned to modify the gain or the offset of the individual pixels.

9. A method for operating a spectroscopic sensor device, the spectroscopic sensor including an absorption path for receiving at least one fluid medium that is to be analyzed, an infrared radiation source for sending out infrared radiation into the absorption path, an infrared sensor array that has a multiplicity of pixels that can be individually evaluated, which are fashioned to detect the infrared radiation propagated from the infrared radiation source through the fluid medium as individual pixel measurement signals, the pixels of one or more pixel regions of the infrared sensor array being provided at least partly with a respective optical filter for the wavelength-selective transmission of the infrared radiation, and an evaluation device that is fashioned to combine a multiplicity of pixel measurement signals of the pixels and to output them via an individual measurement channel, the evaluation device being fashioned to determine the position of the optical filter or filters, the method comprising:

measuring the pixel measurement signals of the pixels in one or more pixel regions having in each case a multiplicity of pixels of the infrared sensor array;

analyzing the pixel measurement signals on the basis of at least one specified criterion;

determining a position of the optical filter or filters by the evaluation device; and combining the pixel measurement signals of the individual pixels in a respective region, taking into account the result of the analysis.

* * * * *